United States Patent [19]

Mizusaki et al.

[11] Patent Number: 4,877,909

[45] Date of Patent: Oct. 31, 1989

[54] PROCESS FOR REDUCING ALDEHYDES OR KETONES

[75] Inventors: Sigenobu Mizusaki; Hajime Matsushita; Shigeo Ishiguro; Hiroshi Ichinose, all of Yokohama; Akira Izumi, Kyoto, all of Japan

[73] Assignee: Japan Tobacco, Inc., Tokyo, Japan

[21] Appl. No.: 126,106

[22] PCT Filed: Sep. 10, 1986

[86] PCT No.: PCT/JP86/00460

§ 371 Date: Feb. 22, 1988

§ 102(e) Date: Feb. 22, 1988

[87] PCT Pub. No.: WO88/01995

PCT Pub. Date: Mar. 24, 1988

[51] Int. Cl.$^4$ .................. C07C 29/132; C07C 29/14
[52] U.S. Cl. ................................. 568/880; 568/814; 568/830; 568/846; 568/862
[58] Field of Search ............... 568/485, 487, 814, 830, 568/846, 880

[56] References Cited

PUBLICATIONS

Mehrotra et al, Indian Journal of Chemistry, vol. 11, No. 8, (1973) pp. 814–816.

Ishii et al, Jour. of Organic Chemistry, vol. 51, No. 2 (1986) pp. 240–242.

Nondek et al., "Collection of Czechoslovak Chemical Comm"., vol. 45, No. 7, (1980) pp. 1937–1939.

*Primary Examiner*—Werren B. Lone

[57] ABSTRACT

A process for reducing an aldehyde or ketone in the presence of a stable, highly active catalyst which is insoluble in a solvent and which can be recovered easily from the reaction system after completion of the reaction and used repeatedly, characterized in that an aldehyde or ketone having a carbonyl group is reacted with an alcohol in the presence of hydrous zirconium oxide as the catalyst.

19 Claims, No Drawings

PROCESS FOR REDUCING ALDEHYDES OR KETONES

DESCRIPTION

1. Technical Field

The present invention relates to a new advantageous process for reducing an aldehyde or ketone into a corresponding alcohol with isopropyl alcohol in the presence of a catalyst.

2. Background Art

When an aldehyde or ketone is treated with a metal alkoxide and an alcohol, reduction occurs to form an alcohol corresponding to the aldehyde or ketone. This reaction is well known and it is usually called "Meerwein-Ponndorf reduction" (cf. A. L. Wilds, Org. React., 2, 178 (1944). Various combinations of a metal alcoholate with an alcohol have been investigated heretofore. Among them, a combination of aluminum isopropoxide with isopropyl alcohol is employed usually, since side reactions such as aldol condensation scarcely occur in the presence thereof, it is soluble not only in alcohols but also in hydrocarbons to make a homogeneous reaction possible and the reaction proceeds rapidly in the presence thereof to form a reduction product usually in a high yield. In this reaction, hydrogen atoms are directly transferred from the alcohol into the carbonyl group of the aldehyde or ketone in the presence of aluminum and aluminum isopropoxide acts as the catalyst. This combination can be employed in the reduction of several milligrams to several hundred grams of an aldehyde or ketone, since the reaction system is simple, the reactants are relatively safe and inexpensive and the reaction proceeds under mild conditions.

However, since the reaction in the conventional process is a homogeneous reaction, troublesome operations such as hydrolysis, extraction with an organic solvent, dehydration and distillation are necessitated for isolating the product after completion of the reaction. Further, since the carbonyl group is converted into the hydroxyl group, the product has an increased hydrophilic property and, therefore, a loss thereof in the extraction from the aqueous phase with an organic solvent is large. Although aluminum isopropoxide is active in the form of mainly its timer, commercially available aluminum isopropoxide or crystalline aluminum isopropoxide is in the form of its tetramer having a low reactivity. Under these circumstances, it is recommended that the catalyst is prepared immediately before use in the reduction.

In addition, the catalyst must be stored carefully, since it is gradually hydrolyzed by water in air to form the alcohol and aluminum hydroxide. After completion of the reaction, the catalyst is hydrolyzed so as to isolate the product from the reaction system. The process has a problem that the catalyst cannot, therefore, be used repeatedly and is discharged wastefully.

3. Disclosure of Invention

An object of the present invention is to provide a catalyst which is stable, highly active and insoluble in a solvent, which can be removed easily from the reaction system after completion of the reaction and which can be used repeatedly.

The present invention provides a process for reducing an aldehyde or ketone characterized in that hydrous zirconium oxide is used in place of a metal alcoholate (mostly aluminum isopropoxide) used heretofore. The inventors were interested in the fact that alcohols are adsorbed to stable hydrous zirconium oxide and, after investigations, the inventors have found that the hydroxyl group of the hydrous zirconium oxide is converted into an alkoxyl group. The present invention has been completed on the basis of this finding.

According to the reduction process of the present invention, an aldehyde or ketone is converted into a corresponding alcohol in a high yield while by-products are formed in only a small amount. Particularly, in a liquid phase reaction, a product having a sufficiently high purity can be obtained by merely filtering off the hydrous zirconium oxide and distilling off the solvent. In a gas phase reaction, the reaction can be conducted either continuously or batchwise and the product can be isolated easily in the same manner as in the liquid-phase reaction.

Hydrous zirconium oxide can be used advantageously, since it necessitates no pretreatment before the reaction, it is insoluble not only in water but also in organic solvents to make the repeated use after recovery possible and, therefore, no industrial waste is formed.

4. Best Mode for Carrying Out the Invention

Hydrous zirconium oxide to be used in the present invention can be produced at a low cost from zircon sand or baddeleyite present in a large amount as mineral sources on the earth via zirconium oxychloride ($ZrOCl_2 \cdot 8H_2O$). More particularly, when an aqueous alkali solution is added gradually to an aqueous zirconium oxychloride solution, the zirconium oxychloride is decomposed to precipitate a microgel of hydrous zirconium oxide. The pH of the reaction system is adjusted to 6 to 7 and the reaction mixture is filtered to remove an aqueous solution of excessive acids. As a result, the microgel is converted into an elastic mass of the gel. The gel is washed with deionized water, cut into pieces of a suitable size, spread on a glass plate and air-dried to form translucent white hard amorphous product. This product is stable in water, alcohol and many other solvents and is ion-exchangeable with various metal ions. Alcohols are adsorbed to the amorphous product. The obtained hydrous zirconium oxide is dried by heating at about 80° C. under reduced pressure and classified to obtain a reaction catalyst.

The reaction may be regarded as conducted in the similar manner as in a known process for the reduction of an aldehyde or ketone in liquid phase with a metal alkoxide and an alcohol except that the metal alkoxide is replaced with hydrous zirconium oxide. Techniques ordinarily employed in the known process such as distillation of acetone, i.e. by-product, so as to complete the reaction rapidly can be employed in the process of the present invention. In conducting the reaction, hydrous zirconium oxide is added in an amount of 0.1 to 10 g, preferably 1 to 3 g, per mmol of the aldehyde or ketone, to 0.5 to 10 ml, preferably 1 to 3 ml, of isopropyl alcohol and the mixture is heated. It is preferred in accelerating the reaction to distill by-product acetone in the course of the reaction. After completion of the reaction, hydrous zirconium oxide is removed by filtration and the filtrate is distilled as it is or, alternatively, the solvent is distilled off to form crystals of the intended product. The used hydrous zirconium oxide is washed with ethanol and then with water to remove powders therefrom and dried to recover hydrous zirconium oxide ready for reuse.

Hydrous zirconium oxide which is in a highly active, stable hard amorphous form can be used also in a gas-phase reaction. In this case, a reaction tube packed with hydrous zirconium oxide is heated to 70° to 200° C., preferably 75° to 110° C. and then isopropyl alcohol and an aldehyde or ketone gasified by heating are continuously fed thereinto together with a carrier gas such as air, nitrogen, helium or argon.

The outlet of the reaction tube is cooled with a refrigerant such as water or ice to condense the product, and unreacted isopropyl alcohol and acetone. The product can be isolated in the same manner as in the above-mentioned liquid-phase reaction.

The following examples will further illustrate the present invention, which by no means limit the invention, since various modifications are possible without departing from the gist of the invention.

EXAMPLE 1

200 g of zirconiumoxychloride (octahydrate) was dissolved in 10 l of deionized water. The pH of the solution was adjusted to 6.80 by slowly adding 1 N aqueous sodium hydroxide solution under stirring. A hydrate gel thus formed was filtered to separate an aqueous solution of excess salts. The gel was washed with deionized water repeatedly until chloride ion was no more detected in the wash water. The gel was cut into small pieces with a knife, spread on a glass plate and dried to obtain 90 g of hydrous zirconium oxide. A 14- to 20-mesh fraction of the obtained hydrous zirconiumoxide dried at 80° C. under reduced pressure for 1 h. 10 g of the dried product was taken up and placed in a 100-ml flask provided with a reflux condenser together with 10 ml of isopropyl alcohol and 911 mg (5 mmol) of benzophenone and refluxed gently. The reaction procedure was followed up according to gas chromatography. 53% of the starting material disappeared after 3 h and 100% thereof disappeared after 10 h. A peak of the corresponding alcohol was observed. The reaction mixture was cooled to room temperature and filtered through a glass filter (G 3). Hydrous zirconium oxide was washed thoroughly with ethanol. The filtrate was combined with the washing and the solvents were distilled off therefrom in a rotary evaporator to obtain crude crystals. After recrystallization from petroleum ether, 905 mg of acicular crystals were obtained. yield: 98 %.

Recovered hydrous zirconium oxide was washed thoroughly with hot ethanol on a glass filter (G 3), transferred into a 500-ml beaker and washed with water. Fine suspending material was removed by decantation and the residue was filtered. After air-drying at room temperature followed by heat treatment conducted at 80° C. under reduced pressure for 1 h, 9.8 g of hydrous zirconium oxide was obtained in the form of a white translucent amorphous substance. Fresh hydrous zirconium oxide was supplied thereto to a total amount of 10 g. It was used again in the reduction of benzophenone to obtain a reduction product in a yield of 97%.

EXAMPLE 2

10 g of hydrous zirconium oxide dried at 80° C. under reduced pressure for 1 h, 5 mmol of an aldehyde or ketone and 10 ml of isopropyl alcohol were placed in a 100-ml flash provided with a reflux condenser and heated under gentle reflux. The progress of the reaction was followed up by subjecting a portion of the reaction solution directly to gas chromatography.

After completion of the reaction, hydrous zirconium oxide was recovered by filtration and washed with 5 ml of isopropyl alcohol or ethanol. The filtrate was combined with the washing and the solvents were distilled off. The residue comprised a substantially pure product. If necessary, the product was purified by distillation or crystallization.

TABLE 1

| | Aldehyde or ketone | Reaction time (h) | Reaction product | Yield according to gas chromatography (%) | Per-pass yield (%) |
|---|---|---|---|---|---|
| 1. | $CH_3CH_2\overset{\underset{\mid}{CH_3}}{C}HCHO$ | 1 | $CH_3CH_2\overset{\underset{\mid}{CH_3}}{C}HCH_2OH$ | 100 | — |
| 2. | $CH_3(CH_2)_4CHO$ | 1 | $CH_3(CH_2)_5OH$ | 83 | 79 |
| 3. | $CH_3(CH_2)_8CHO$ | 1.5 | $CH_3(CH_2)_9OH$ | 72 | 70 |
| 4. | 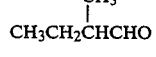 | 1 | 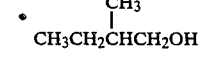 | 43 | 42 |
| 5. | 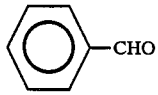 | 5 | 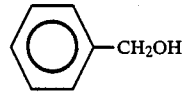 | 88 | 87 |
| 6. | 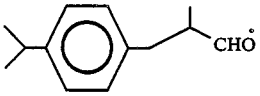 | 2 | 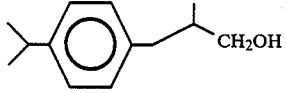 | 98 | 96 |
| 7. | 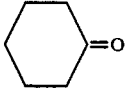 | 12 | 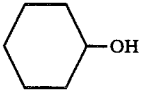 | 100 | 98 |

TABLE 1-continued

| | Aldehyde or ketone | Reaction time (h) | Reaction product | Yield according to gas chromatography (%) | Per-pass yield (%) |
|---|---|---|---|---|---|
| 8. | CH$_3$(CH$_2$)$_6$$\overset{\text{O}}{\overset{\|}{\text{C}}}$CH$_2$CH$_3$ | 24 | CH$_3$(CH$_2$)$_6$$\overset{\text{OH}}{\overset{\|}{\text{C}}}$HCH$_2$CH$_3$ | 100 | 98 |
| 9. | CH$_3$(CH$_2$)$_3$$\overset{\text{O}}{\overset{\|}{\text{C}}}$CH$_3$ | 5 | CH$_3$(CH$_2$)$_3$$\overset{\text{OH}}{\overset{\|}{\text{C}}}$HCH$_3$ | 100 | 94 |
| 10. | 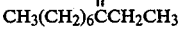 | 2 | 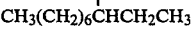 | 100 | 95 |
| 11. | CH$_3$CH$_2$$\overset{\text{O}}{\overset{\|}{\text{C}}}$CH$_2$CH$_3$ | 10 | CH$_3$CH$_2$$\overset{\text{OH}}{\overset{\|}{\underset{\underset{\text{H}}{\|}}{\text{C}}}}$CH$_2$CH$_3$ | 100 | — |
| 12. | 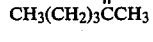 | 1 | 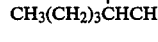 | 100 | 100 |
| 13. | 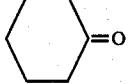 | 10 |  | 100 | 96 |
| 14. | CH$_3$(CH$_2$)$_2$CHO | 1 | CH$_3$(CH$_2$)$_3$CH | 80 | — |
| 15. | $\overset{\text{CH}_3}{\overset{\|}{\text{CH}_3\text{CHCHO}}}$ | 1 | $\overset{\text{CH}_3}{\overset{\|}{\text{CH}_3\text{CHCH}_2\text{OH}}}$ | 100 | — |

The kind of the aldehyde or ketone, i.e. hydrocarbon aldehyde or ketone such as unsubstituted aliphatic and aromatic aldehydes and ketones, that had been reacted, plus the reaction time, reaction product and yield are shown in Table 1.

EXAMPLE 3

1 g of hydrous zirconium oxide (14- to 20-mesh) was placed in a glass tube having an inner diameter of 4 mm and both ends of the tube were stopped with quartz wool to form a catalyst bed. The catalyst bed portion of the glass tube was placed in a constant temperature bath kept at 90° C. and the inlet and outlet portions thereof were arranged so that they could be heated with a ribbon heater to prevent the reactants and the product from condensing. Nitrogen gas passed through isopropyl alcohol heated to 70° C. was introduced thereinto through the inlet. After leaving the tube to stand for 1 h, nitrogen gas passed through cyclohexanone heated to 120° C. was also introduced thereinto. The flow rate was 30 ml/min. A given amount of the product was taken at the outlet and its composition was examined according to gas chromatography to reveal that the conversion and the selectivity were both 100 % in a stationary state.

EXAMPLE 4

1 g of hydrous zirconium oxide (14- to 20-mesh) was placed in a glass tube having an inner diameter of 4 mm and both ends of the tube were stopped with quartz wool to form a catalyst bed. The catalyst bed portion of the glass tube was placed in a constanttemperature bath kept at 90° C. and the inlet and outlet portions thereof were arranged so that they could be heated with a ribbon heater to prevent the reactants and the product from condensing. Nitrogen gas passed through isopropyl alcohol heated to 70° C. was introduced thereinto through the inlet. After leaving the tube to stand for 1 h, 2 mmol (379 μl) of 3-decanone was injected thereinto through the inlet by means of a syringe. The flow rate determined at the outlet was 37.5 ml/min. When the total amount of the liquid thus obtained reached 25 ml, the elution of substances other than isopropyl alcohol was no more recognized. According to gas chromatography, the yield of 3-decanol, the intended product, was 97% and unreacted 3-decanone was not recognized.

What is claim is:

1. Process for reducing an aldehyde or ketone to the corresponding alcohol, which comprises reacting at a temperature of about 70° to 200° C. an aldehyde or ketone selected from the group consisting of unsubstituted aliphatic or aromatic aldehydes and ketones, with isopropyl alcohol in the presence of a solid catalyst, prepared by partially dehydrating zirconium oxide to form said catalyst, to reduce directly the aldehyde or ketone and thereby form the corresponding alcohol from the aldehyde or ketone.

2. Process of claim 1 wherein the direct reduction is a liquid-phase reaction.

3. Process of claim 1 wherein the direct reduction is a gas-phase reaction.

4. Process of claim 1 wherein the direct reduction is effected, and the formed corresponding alcohol and solid catalyst are separated from each other, all in the absence of hydrolysis.

5. Process of claim 4 wherein the direct reduction is a liquid-phase reaction, and the solid catalyst is separated from the liquid phase by filtration.

6. Process of claim 4 wherein the direct reduction is a gas-phase reaction, and the gas phase is separated from the solid catalyst by drawing off and condensing the gas phase.

7. Process of claim 1 wherein the formed corresponding alcohol and the solid catalyst are separated from each other, and the solid catalyst is recycled and the reaction repeated.

8. Process of claim 1 wherein said catalyst, aldehyde or ketone and isopropyl alcohol are used in relative amounts corresponding to about 0.1–10 g of said catalyst per mmol of said aldehyde or ketone and per 0.5–10 ml of said isopropyl alcohol.

9. Process for reducing an aldehyde or ketone to the corresponding alcohol, which comprises reacting at a temperature of about 70° to 200° C. a carbonyl group containing hydrocarbon aldehyde or ketone with isopropyl alcohol in the presence of a solid catalyst, prepared by partially dehydating zirconium oxide to form said catalyst, to reduce directly the carbonyl group of the aldehyde or ketone and thereby form the corresponding alcohol from the aldehyde or ketone.

10. Process of claim 9 wherein the reaction is carried out as a liquid-phase reaction.

11. Process of claim 9 wherein the reaction is carried out as a gas-phase reaction.

12. Process of claim 9 wherein the reaction is carried out as a liquid-phase reaction in a liquid phase consisting of the aldehyde or ketone and the isopropyl alcohol which is reacted therewith.

13. Process of claim 9 wherein the reaction is carried out as a gas-phase reaction in a gas phase consisting of a carrier gas containing the aldehyde or ketone and the isopropyl alcohol which is reacted therewith.

14. Process of claim 9 wherein said catalyst is used in water insoluble, organic solvent insoluble, and alcohol adsorbing, dry, highly reactive, stable hard amorphouse form.

15. Process of claim 14 wherein said catalyst is prepared by decomposing zirconium oxychloride with alkali in aqueous solution to precipitate a microgel of hydrous zirconium oxide, and recovering, washing and drying the precipitated hydrous zirconium oxide.

16. Process of claim 9 wherein said catalyst, aldehyde or ketone and isopropyl alcohol are used in relative amounts corresponding to about 0.1–10 g of said catalyst per mmol of said aldehyde or ketone and per 0.514 10 ml of said isopropyl alcohol.

17. Process for reducing an aldehyde or ketone to the corresponding alcohol, which comprises reacting at a temperature of about 70° to 200° C. a carbonyl group containing hydrocarbon aldehyde or ketone with isopropyl alcohol in the presence of a solid catalyst, prepared by partially dehydrating zirconium oxide to form said catalyst, to reduce directly the carbonly group of the aldehyde or ketone and thereby form the corresponding alcohol from the aldehyde or ketone, the direct reduction being effected, and the formed corresponding alcohol and the solid catalyst being separated from each other, all in the absence of hydrolysis, and the solid catalyst being recycled and the reaction repeated.

18. Process of claim 17 wherein said catalyst, aldehyde or ketone and isopropyl alcohol are used in relative amounts corresponding to about 0.1–10 g of said catalyst per mmol of said aldehyde or ketone and per 0.5–10 ml of said isopropyl alcohol.

19. Process of claim 17 wherein said catalyst is used in water insoluble, organic solvent insoluble, and alcohol adsorbing, dry, highly reactive, stable hard amorphous form.

* * * * *